United States Patent [19]
Zimmer et al.

[11] Patent Number: 6,004,963
[45] Date of Patent: Dec. 21, 1999

[54] SUBSTITUTED 2, 4-IMIDAZOLIDINEDIONE COMPOUNDS AS PHARMACEUTICAL ACTIVE INGREDIENTS

[75] Inventors: Oswald Zimmer, Wuerselen; Hoerst Boehlke, Stolberg; Stephan Wnendt, Aachen; Cornelia Geist, Roetgen; Kai Zwingenberger, Aachen, all of Germany

[73] Assignee: Gruenenthal GmbH, Aachen, Germany

[21] Appl. No.: 08/738,232

[22] Filed: Oct. 25, 1996

[30] Foreign Application Priority Data

Oct. 27, 1995 [DE] Germany .......................... 195 40 027

[51] Int. Cl.⁶ ...................... C07D 403/00; C07D 417/04; A61K 31/41; A61K 31/425
[52] U.S. Cl. .......................... 514/255; 514/363; 514/365; 514/336; 514/374; 514/378; 514/397; 514/341; 544/359; 544/366; 548/147; 548/137; 548/196; 548/240; 546/268.1; 546/268.4; 546/272.7
[58] Field of Search ..................................... 548/147, 196, 548/137, 240; 514/365, 378, 397, 336, 374, 363, 255, 341; 546/268.1, 268.4, 272.7; 544/359, 366

[56] References Cited

U.S. PATENT DOCUMENTS

| | | | |
|---|---|---|---|
| 4,746,669 | 5/1988 | Caldwell et al. | 514/342 |
| 4,944,791 | 7/1990 | Schroder et al. | 71/92 |

FOREIGN PATENT DOCUMENTS

| | | |
|---|---|---|
| 363061 | 4/1990 | European Pat. Off. |
| WO 92/07567 | 5/1992 | WIPO . |
| WO 95/02591 | 1/1995 | WIPO . |

OTHER PUBLICATIONS

Peng et al., "Potential Central Nervous System Antitumor Agents, Hydantoin Derivatives", *Journal of Medicinal Chemistry*, 1975, vol. 18, No. 8, pp. 846–849.

Oldfield et al., "The Chemistry and Pharmacology of a Series of Cycloalkanespiro–5'–hydantoins", *J. Med. Chem.*, vol. 8, pp. 239–249 (1965).

Clauss et al., "Modulation of Endothelial Cell Hemostatic Properties by TNF: Insights Into the Role of Endothelium in the Host Response to Inflammatory Stimuli", *Tumor Necrosis Factors: The Molecules and Their Emerging Role in Medicine*, edited by Bruce Beutler, Raven Press, Ltd., New York, pp. 49–63, (1992).

Satsangi et al., "1–(4–Substituted–thiazol–2–yl) hydantoins as Anti–inflammatory and CNS–Active Agents", *Pharmazie*, vol. 38, pp. 341–342 (1983).

Woehrmann et al., "Local Skin Reactivity After Induction of Shwartzman Reaction in Rabbits", *Exp. Toxic. Pathol.*, 47, pp. 167–172 (1995).

Cortes et al., "Effect of Structural Modification of the Hydantoin Ring on Anticonvulsant Activity", *J. Med. Chem.*, 28, pp. 601–606 (1985).

Angew, *Chem.*, vol. 73, p. 66 (1961).

Waser et al., "Die Entwicklung neuer Antiepiliptika", *Arzneim. Forsch/Drug Res.*, 27(II), pp. 1942–1953 (1977).

Fischer et al., "Investigation of the Antitumor Activity of New Epoxide Derivatives", *Arzneim. Forsch/Drug Res.*, 34 (I), pp. 663–668 (1984).

*Primary Examiner*—Jose' G. Dees
*Assistant Examiner*—Sabiha N. Qazi
*Attorney, Agent, or Firm*—Evenson, McKeown, Edwards & Lenahan, P.L.L.C.

[57] ABSTRACT

A substituted 2,4-imidazolidinedione compound corresponding to the formula I

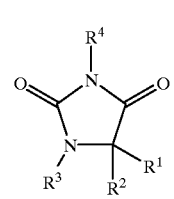

I a process for production thereof and the use of these compounds in a pharmaceutical preparation are described. Substituents R1, R2, R3 and R4 have the same meaning as defined in the specification.

9 Claims, No Drawings

SUBSTITUTED 2, 4-IMIDAZOLIDINEDIONE COMPOUNDS AS PHARMACEUTICAL ACTIVE INGREDIENTS

This invention relates to substituted 2,4-imidazolidinedione compounds, to a process for the production thereof and to the use of these compounds in pharmaceutical preparations.

Excessive formation of the cytotoxic tumour necrosis factor α (TNF-α) plays a central part in the pathogenesis of many serious disorders. These disorders include multiple sclerosis, graft-versus-host syndrome, transplant rejection, aphthous stomatitis, erythema nodosum leprosum, Boeck's disease, rheumatoid arthritis and a series of other disorders accompanied by inflammatory symptoms. One therapeutic approach to these disorders involves general suppression of the release of TNF-α by immunomodulators having a suppressive nature, for example dexamethasone.

However, in disorders with leucocyte-dominated vasculitis involving post-capillary venules, for example aphthous stomatitis, cutaneous lupus erythematosus, gangrenous pyoderma and orogenital ulcers in Behget's disease, focused intervention is preferable in order to avoid the disadvantages of general immunosuppression.

Endogenic mediators acting on the endothelium and circulating leucocytes are pathogenic factors in these disorders. Local release of TNF-α and other cytokines results in a focused increase in the adhesiveness of the endothelium towards leucocytes, which makes a major contribution to the formation of vasculitis [M. Clauss et al. in *Tumour Necrosis Factors*, editor: B. Beutler, Raven New York 1992, pp. 49–64]. Substances which, by means of focused intervention, are capable of suppressing the change in the endothelium without simultaneously blocking the specific cellular immune defences are superior to general immunosuppressors, such as dexamethasone, and may provide novel therapeutic options.

The class of hydantoin compounds, to which the compounds according to the invention also belong, has been intensively researched in the past. Many derivatives have been synthesised, which have applications, for example, in cosmetic articles, are used as insecticides or herbicides or constitute the basis of epoxy resins.

In the pharmaceuticals sector, hydantoin compounds are known in particular to have anticonvulsive, anti-inflammatory [*J. Med. Chem.* 8, 239 (1965); *Arzneim. Forsch./Drug Res.* 27(II), 1942 (1977); *Pharmazie* 38, 341 (1983); *J. Med. Chem.* 28, 601, (1985)] and antineoplastic activity [*J. Med. Chem.* 18, 846 (1975), *Arzneim. Forsch./Drug Res.* 34(I), 663, (1984)].

The object underlying the present invention was the development of novel, stable immunomodulators which do not bring about general immunosuppression. The substances developed should furthermore have an antivasculitic action.

It has now been found that the requirements set for the substances to be developed are fulfilled by certain substituted 2,4-imidazolidinedione compounds. These compounds, which belong to the class of the hydantoins, are distinguished by a strong immunomodulatory action. They suppress the release of TNF-α, without simultaneously resulting in a general blocking of cellular immune defences. The compounds according to the invention also exhibit an antivasculitic action, which is not exclusively attributable to the inhibition of TNF-α release.

The present invention accordingly provides substituted 2,4-imidazolidinedione compounds of the formula I

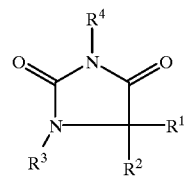

in which
$R^1$ means $C_{1-6}$ alkyl or $C_{3-6}$ cycloalkyl,
$R^2$ means $C_{1-6}$ alkyl, phenyl, —$(CH_2)_{1-3}$-phenyl or —$(CH_2)_{1-4}$—$COOR^5$ or
$R^1$ and $R^2$ together mean —$(CH_2)_{4-6}$-, —$(CH_2)_2$—O—$(CH_2)_2$- or

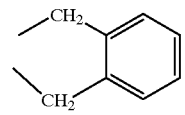

$R^3$ means H, $C_{1-5}$ alkyl or —$(CH_2)_{1-4}$—$COOR^5$,
$R^4$ is a heteroaromatic selected from the group of the formulae

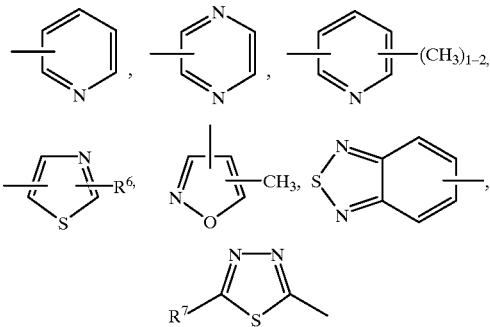

$R^5$ denotes $C_{1-3}$ alkyl,
$R^6$ means H, $C_{1-4}$ alkyl, phenyl or benzyl and
$R^7$ means H, $C_{1-4}$ alkyl or trifluoromethyl.

Preferred substituted 2,4-imidazolidinedione compounds are of the formula I, in which
$R^1$ means $C_{1-4}$ alkyl or $C_{3-4}$ cycloalkyl,
$R^2$ $C_{3-6}$ alkyl, phenyl, —$(CH_2)_{1-2}$-phenyl or —$(CH_2)_{1-2}$—$COOR^5$, or
$R^1$ and $R^2$ together mean —$(CH_2)_5$- or

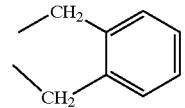

$R^3$ means H, $C_{1-4}$ alkyl or —$(CH_2)_{1-2}$—$COOR^5$,
$R^4$ is a heteroaromatic selected from the group of the formulae

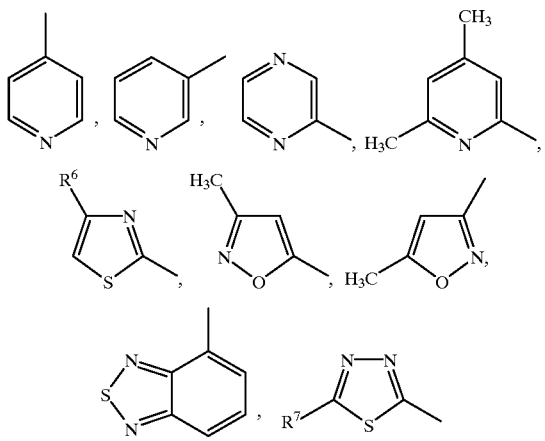

$R^5$ denotes $C_{1-3}$ alkyl,
$R^6$ means H or phenyl and
$R^7$ means H, methyl, tert.-butyl or trifluoromethyl.

Particularly preferred compounds of the formula I are those in which $R^1$ is ethyl or cyclobutyl, $R^2$ is phenyl or $R^1$ and $R^2$ together mean —$(CH_2)_5$- . Compounds of the formula I in which $R^1$ and $R^2$ together denote —$(CH_2)_5$- are in particular preferred.

Further particularly preferred compounds of the formula I are those in which $R_3$ is H, $C_{1-3}$ alkyl or —$CH_2$—$COOR^5$ and $R^5$ means ethyl. Compounds of the formula I in which $R^3$ is H are in particular preferred.

Particularly preferred compounds of the formula I are moreover those in which $R^4$ is a heteroaromatic selected from the group pyridin-4-yl, pyridin-3-yl, thiazol-2-yl, 3-methylisoxazol-5-yl or 5-methylisoxazol-3-yl. Compounds of the formula I in which $R^4$ of the heteroaromatic is thiazol-2-yl are in particular preferred.

The present invention also provides a process for the production of a substituted 2,4-imidazolidinedione compound of the formula I, in which
$R^1$ means $C_{1-6}$ alkyl or $C_{3-6}$ cycloalkyl,
$R^2$ means $C_{1-6}$ alkyl, phenyl, —$(CH_2)_{1-3}$-phenyl or —$(CH_2)_{1-4}$ —$COOR^5$ or
$R^1$ and $R^2$ together mean —$(CH_2)_{4-6}$-, —$(CH_2)_2$—O— $(CH_2)_2$- or

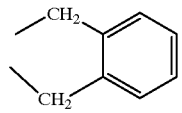

$R^3$ means H, $C_{1-5}$ alkyl or -$(CH_2)_{1-4}$—$COOR^5$,
$R^4$ is a heteroaromatic selected from the group of the formulae

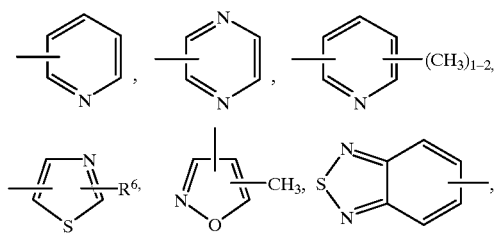

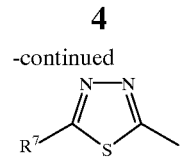

$R^5$ denotes $C_{1-3}$ alkyl,
$R^6$ means H, $C_{1-4}$ alkyl, phenyl or benzyl and
$R^7$ means H, $C_{1-4}$ alkyl or trifluoromethyl,
wherein the process is characterised in that 1,1'-carbonyldiimidazole or diphenyl carbonate are added to an amine of the formula II
$R^4$—$NH_2$
and then reacted with a compound of the formula III

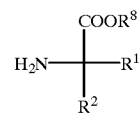

in which $R^8$ denotes H or $C_{1-3}$ alkyl to yield a compound of the formula I in which $R^3$ means H, which compound is then, if desired, deprotonated and then reacted with a compound of the formula IV
X—$C_{1-5}$ alkyl
or a compound of the formula V
X—$(CH_2)_{1-4}$—$COOR^5$
in which X means Cl, Br or I, to yield a compound of the formula I in which $R^3$ means $C_{1-5}$ alkyl or —$(CH_2)_{1-4}$—$COOR^5$.

The reaction of an amine of the formula II with 1,1'-carbonyldiimidazole or diphenyl carbonate is performed in a manner known per se [*Angew. Chem.*, 73, 66 (1961)]. The subsequent reaction with an amino acid ester of the formula III to yield a compound of the formula I, in which $R^3$ is H, is preferably performed in aprotic solvents, such as ethers, for example diethyl ether or tetrahydrofuran, or in aromatic hydrocarbons, for example toluene, chlorobenzene or 1,2-dichlorobenzene, at temperature of between 20° C. and 180° C. In this reaction, in addition to the compound of the formula I, in which $R^3$ is H, the corresponding urea derivative of the formula VI

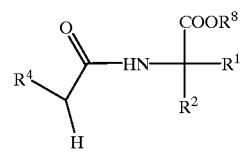

may also be formed. A compound of the formula VI, in which $R^8$ is H, may be converted into a compound of the formula I, in which $R^3$ is H, by reaction with thionyl chloride. A compound of the formula VI, in which $R^8$ is $C_{1-3}$ alkyl, is subjected to alkaline saponification before cyclisation to yield a compound of the formula I, in which $R^3$ is H, or is directly converted into a compound of the formula I, in which $R^3$ is H, by heating with hydrochloric acid.

In order to produce a compound of the formula I, in which $R^3$ means $C_{1-5}$ alkyl or —$(CH_2)_{1-4}$—$COOR^5$, a compound of the formula I, in which $R^3$ is H, is preferably deprotonated with sodium hydride in dimethylformamide or tetrahydrofuran. The subsequent reaction with a compound of the formula IV or V is performed at temperatures of between 20° C. and 50° C.

The amino acid ester of the formula III required for the production of a compound of the formula I may be produced by esterifying the corresponding amino acid, for example by means of hydrogen chloride solutions in the corresponding alcohol or by heating with the corresponding alcohol with acid catalysis, for example with sulphuric or phosphoric acid.

Another option for obtaining a compound of the formula III is to react an amino acid ester of the formula VII

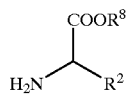

with benzaldehyde to yield a compound of the formula VIII,

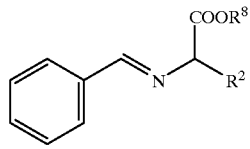

which, once deprotonated with a base, preferably lithium diisopropylamide, is alkylated in ethers or hydrocarbons, for example diethyl ether, tetrahydrofuran or benzene, with a compound of the formula IX,

X—R$^1$ in which X means Cl, Br or I. The benzylidene group is then eliminated under the action of acids.

The compounds according to the invention are toxicologically safe and are thus suitable as pharmaceutical active ingredients. The present invention accordingly also provides the use of a substituted 2,4-imidazolidinedione compound of the formula I as an active ingredient in pharmaceutical preparations, preferably as immunomodulators or in pharmaceutical preparations having an antivasculitic action.

In addition to at least one substituted 2,4-imidazolidinedione compound of the formula I, pharmaceutical preparations according to the invention contain excipients, extenders, solvents, diluents, dyes and/or binders. Selection of the auxiliary substances and the quantities to be used are dependent upon whether the pharmaceutical preparation is to be administered orally, intravenously, intraperitoneally, intradermally, intramuscularly, intranasally, buccally or locally. Suitable preparations for oral administration are tablets, chewable tablets, coated pills, capsules, granules, drops, liquors or syrups, while solutions, suspensions, readily reconstitutible dry preparations and sprays are suitable for parenteral, topical and inhalatory administration. Compounds according to the invention in a depot in dissolved form, on a backing film or dressing, optionally with the addition of agents promoting skin penetration, are examples of suitable percutaneous administration forms. Release of the compounds according to the invention from orally or percutaneously administrable preparation may be delayed.

The quantity of active ingredient to be administered to the patient varies as a function of the patient's weight, the type of administration, the indication and severity of the disorder. Conventionally, 1 to 150 mg per kg of at least one substituted 2,4-imidazolidinedione compound of the formula I is administered.

EXAMPLES

Silica gel 60 (0.040–0.0063 mm) supplied by E. Merck, Darmstadt, was used as the stationary phase for the column chromatography.

Mixing ratios for the eluents for the chromatographic procedures are always stated as volume/volume.

Racemates were resolved on a Chiracel OD column supplied by Daicel Chemical Industries Ltd..

"mp" means "melting point", "RT" means "room temperature" and "of th." means "of theoretical".

Production of Compounds According to the Invention

EXAMPLE 1A

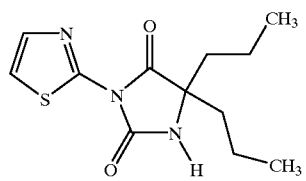

5,5-Dipropyl-3-thiazol-2-yl-2,4-imidazolidinedione

Stage 1

2-Amino-entanoic acid ethyl ester

A suspension of 11.72 g of DL-norvaline in 90 ml of ethanol was combined with 3.6 ml of concentrated sulphuric acid and the mixture refluxed for eight days. A clear solution was formed, from which, after cooling, ethanol was removed by distillation. The residue was redissolved in 200 ml of distilled water and the pH adjusted to a value of between 10 and 12 by adding potassium carbonate. Extraction was then performed three times with 50 ml portions of ethyl acetate, the mixture washed once with 50 ml of a saturated sodium chloride solution and dried over sodium sulphate. Once the solvent had been removed by distillation, 11.93 g of 2-aminopentanoic acid ethyl ester (82% of th.) were obtained in the form of a yellowish oil.

Stage 2

2-(Benzylideneamino)pentanoic acid ethyl ester

A solution of 11.90 g of the product from stage 1 in 150 ml of diethyl ether was combined in succession with 8.3 ml of benzaldehyde, 23 ml of triethylamine and 7.0 g of anhydrous magnesium sulphate. The mixture was stirred for 24 hours at room temperature, then filtered and washed with diethyl ether. Once the solvent had been removed by distillation, 18.40 g of 2-(benzylideneamino)pentanoic acid ethyl ester (96% of th.) were obtained in the form of a yellowish, viscous mass.

Stage 3

2-Amino-2-propylpentanoic acid ethyl ester

A solution of 10.4 ml of diisopropylamine in 200 ml of tetrahydrofuran was combined dropwise at 0° C. with stirring under a stream of dry nitrogen with 49 ml of a 1.6 molar solution of n-butyllithium in n-hexane. After cooling to –78° C., a solution of 18.31 g of the product from stage 2 in 80 ml of tetrahydrofuran was added dropwise. The entire reaction batch was stirred for 30 minutes and a solution of 8.8 ml of 1-iodopropane in 40 ml of tetrahydrofuran was then added dropwise. The reaction batch was stirred for 16 hours, wherein the temperature slowly rose to 20° C. The solvent was removed by distillation. The resultant orange-coloured residue was redissolved in 500 ml of 1 N hydrochloric acid. After 1 hour's stirring at 20° C., extraction was performed three times with 100 ml portions of diethyl ether. The phase acidified with hydrochloric acid was adjusted to a pH of between 10 and 12 with potassium hydroxide and then extracted three times with 100 ml portions of diethyl ether.

The extracts were combined, washed twice with a saturated sodium chloride solution and dried over sodium sulphate. The crude product obtained after removing the solvent by distillation was purified by passage through a silica gel column with ethyl acetate. 9.84 g of 2-amino-2-propylpentanoic acid ethyl ester (67% of th.) were obtained in the form of a slightly coloured oil.

Stage 4
2-Propyl-2-(3-thiazol-2-vlureido)pentanoic acid ethyl ester

A solution of 5.40 g of 2-aminothiazole in 150 ml of tetrahydrofuran was combined at 20° C. with 8.75 g of 1,1'-carbonyldiimidazole and the mixture stirred for 30 minutes. The mixture was then raised within 20 minutes to a bath temperature of between 55 and 60° C. and a solution of 9.80 g of the product from stage 3 in 30 ml of tetrahydrofuran was added dropwise. A clear, red-brown solution was obtained, which was stirred for 60 hours at a temperature of between 55° C. and 60° C. Once the solvent had been removed by distillation, the residue was purified by passage through a silica gel column with ethyl acetate. 10.20 g of 2-propyl-2-(3-thiazol-2-ylureido)pentanoic acid ethyl ester (62% of th.) were obtained in the form of a yellowish oil.

Stage 5
2-Propyl-2-(3-thiazol-2-vlureido)pentanoic acid 10.03 g of the product from stage 4 were dissolved with stirring in 200 ml of semi-concentrated sodium hydroxide solution at a temperature of 20° C. The pH was then adjusted to 4 with concentrated hydrochloric acid and extracted three times with 50 ml portions of dichloromethane. The extracts were washed once with a saturated sodium chloride solution and dried over sodium sulphate. Once the solvent had been removed by distillation, 8.48 g of 2-propyl-2-(3-thiazol-2-ylureido)pentanoic acid (93% of th.) were obtained in the form of white crystals (mp 154–155° C.).

Stage 6
5,5-Dipropyl-3-thiazol-2-vl-2,4-imidazolidinedione 8.28 g of the product from stage 5 were combined with 20 ml of thionyl chloride. The mixture was stirred for 18 hours at 20° C. Ice was then added for the purpose of decomposition, the pH adjusted to an alkaline value with potassium carbonate and extraction performed three times with 20 ml portions of dichloromethane. Once the extracts had been washed with a saturated sodium chloride solution and dried over sodium sulphate, the solvent was removed by distillation. The resultant residue was purified by passage through a silica gel column with ethyl acetate. 5.50 g of 5,5-dipropyl-3-thiazol-2-yl-2,4-imidazolidinedione (71 of th.) were obtained in the form of white crystals (mp 127–128° C.).

EXAMPLE 1B

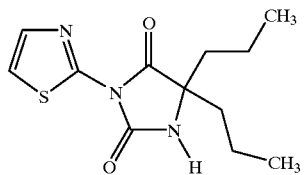

5,5-Dipropyl-3-thiazol-2-yl-2,4-imidazolidinedione 1.71 g of 2-propyl-2-(3-thiazol-2-ylureido)pentanoic acid ethyl ester (product from Example 1A, stage 4) were combined with 30 ml of 30% hydrochloric acid. The mixture was refluxed for three hours. Once the mixture had cooled, the pH was adjusted to an alkaline value with potassium carbonate, extraction was performed three times with ethyl acetate, the mixture washed twice with a saturated common salt solution and dried over sodium sulphate. The crude product obtained by the subsequent removal of the solvent by distillation was purified by passage through a silica gel column with ethyl acetate. 0.62 g of 5,5-dipropyl-3-thiazol-2-yl-2,4-imidazolidinedione (42% of th.) were obtained.

EXAMPLE 2

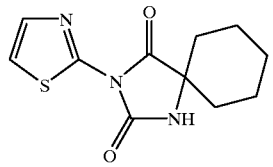

3-Thiazol-2-yl-1,3-diazaspiro[4.5]decane-2,4-dione

Stage 1
1-Amino-1-cyclohexanecarboxylic acid ethyl ester

Under the conditions described in Example 1A, stage 1, 75.5 g of 1-amino-1-cyclohexanecarboxylic acid ethyl ester (80%- of th.) were obtained in the form of a light yellow oil from 100 g of 1-amino-1-cyclohexanecarboxylic acid hydrochloride, 500 ml of ethanol and 20 ml of concentrated sulphuric acid after purification of the crude product by passage through a silica gel column with ethyl acetate/methanol=5/1.

Stage 2
3-Thiazol-2-vl-1,3-diazaspiro[4.5]decane-2 4-dione 44.4 g of 2-aminothiazole, 71.9 g of 1,1'-carbonyldiimidazole and 73.7 g of the product from stage 1 were reacted in accordance with the conditions described in Example 1A, stage 4. The resultant product mixture was purified by passage through a silica gel column with ethyl acetate. 71.8 g of 3-thiazol-2-yl-1,3-diazaspiro-[4.5]decane-2,4-dione (66% of th.) were obtained in the form of white crystals (mp 213–215° C.).

EXAMPLE 3

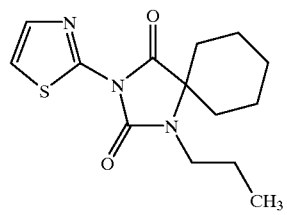

1-Propyl-3-thiazol-2-vl-1,3-diazaspiro[4.5]decane-2,4-dione 5.05 g of the product from Example 2, stage 2 were dissolved in 20 ml of dimethylformamide. 1.10 g of sodium hydride (50% suspension in mineral oil) were added in portions with stirring at 200C. After 1 hour's stirring, 4 ml of 1-iodopropane were added. Stirring was continued for a further 3 hours. The mixture was then diluted with 100 ml of distilled water, extracted three times with 30 ml portions of ethyl acetate, washed with saturated sodium chloride solution and dried over sodium sulphate. Once the solvent had been removed by distillation, the residue was purified by passage through a silica gel column with ethyl acetate/n-hexane=8/5. 3.95 g of l-propyl-3-thiazol-2-yl-1,3-diazaspiro [4.5]decane-2,4-dione (67% of th.) were obtained in the form of white crystals (mp 135–138° C.).

EXAMPLE 4

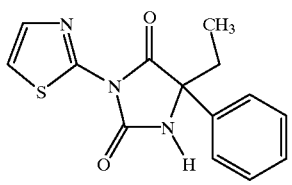

5-Ethyl-5-phenyl-3-thiazol-2-yl-2,4-imidazolidinedione

Stage 1
2-Amino-2-phenylbutyric acid ethyl ester 10.0 g of 2-amino-2-phenylbutyric acid were stirred for 10 days at 30° C. with 140 ml of an ethanolic solution of hydrogen chloride (10l HCl). The ethanol was then removed by distillation, the residue redissolved in 200 ml of distilled water and the pH adjusted to an alkaline value with potassium carbonate. Once the mixture had been extracted three times with ethyl acetate, the extracts dried over sodium sulphate and the solvent removed by distillation, purification was performed by passage through a silica gel column with ethyl acetate. 6.93 g of 2-amino-2-phenylbutyric acid ethyl ester (62% of th.) were obtained in the form of a yellowish oil.

2nd Stage
5-Ethyl-5-phenyl-3-thiazol-2-yl-2,4-imidazolidinedione 2.12 g of 2-aminothiazole, 3.26 g of 1,1'-carbonyldiimidazole and 4.16 g of the product from stage 1 were reacted under the conditions described in Example 1A, stage 4. Once the crude mixture had been purified by passage through a silica gel column with ethyl acetate, 3.90 g of 5-ethyl-5-phenyl-3-thiazol-2-yl-2,4-imidazolidinedione (68% of th.) were obtained in the form of white crystals (mp 150–152° C.).

EXAMPLE 5

(+)- and (−)-5-ethyl-5-phenyl-3-thiazol-2-yl-2,4-imidazolidinedione

Both enantiomers were obtained by resolving the racemate from Example 4 on a chiral HPLC column (mobile solvent: n-hexane/2-propanol=1/1; stationary phase: cellulose tris-3,5-dimethylphenylcarbamate).

EXAMPLE 6

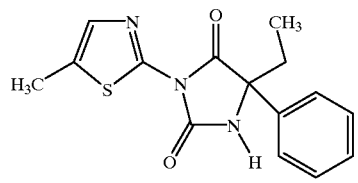

5-Ethyl-3-(5-methyl [1.3.4] thiadiazol-2-yl)-5-phenyl-2,4-imidazolidinedione 2.30 g of 2-amino-5-methyl-1,3,4-thiadiazole were dissolved at room temperature in 40 ml of dry tetrahydrofuran in a nitrogen atmosphere and with exclusion of moisture. 3.24 g of 1,1'-carbonyldiimidazole were then added. The mixture was stirred for 30 minutes at 50° C. 4.15 g of 2-amino-2-phenylbutyric acid ethyl ester (product from Example 3, stage 1) in 10 ml of dry tetrahydrofuran were added dropwise to the resultant suspension and stirred for 20 hours at 50° C. Once the solvent had been removed by distillation, the residue was recrystallised from ethanol. 3.94 g of 5-ethyl-3-(5-methyl[1.3.4]thiadiazol-2-yl)-5-phenyl-2,4-imidazolidinedione (58% of th.) were obtained in the form of white crystals (mp 223–225° C.).

EXAMPLES 7–28

The compounds shown in Table 1 were prepared from the corresponding starting compounds under the conditions described in Examples 1-6.

TABLE 1

| Example | Compound | $R^1$ | $R^2$ | $R^3$ | $R^4$ | mp [° C.] | Prepared in accordance with Example |
|---|---|---|---|---|---|---|---|
| 7 | 5-isopropyl-5-phenyl-3-thiazolyl-2,4-imidazolidinedione | isopropyl | phenyl | H | thiazol-2-yl | 173–175 | 6 |
| 8 | 3-(4-methyl-2,5-dioxo-1-thiazol-2-yl-imidazolidin-4-yl)propionic acid ethyl ester | methyl | 2-ethoxy-carbonyl-ethyl | H | thiazol-2-yl | 88–90 | 6 |
| 9 | 5-isobutyl-5-methyl-3-thiazol-2-yl-2,4-imidazolidinedione | methyl | isobutyl | H | thiazol-2-yl | 138–140 | 6 |
| 11 | 3-thiazol-2-yl-1,3-diazaspiro[4.4]-benzononane-2,4-dione | phenylenedimethyl | | H | thiazol-2-yl | 175–177 | 6 |
| 12 | 5-benzyl-5-methyl-3-thiazol-2-yl-2,4-imidazolidinedione | methyl | benzyl | H | thiazol-2-yl | 197–199 | 1A |
| 13 | 5-methyl-5-pentyl-3-thiazol-2-yl-2,4-imidazolidinedione | methyl | pentyl | H | thiazol-2-yl | 109–111 | 1A |
| 14 | 5-methyl-5-(2-phenyl-ethyl)-3-thiazol-2-yl-2,4-imidazolidine-dione | methyl | 2-phenyl-ethyl | H | thiazol-2-yl | 160–162 | 1A |
| 15 | (2,4-dioxo-3-thiazol-2-yl-1,3-diazaspiro- | pentamethylene | | ethoxy-carbonyl- | thiazol-2-yl | 82–88 | 3 |

TABLE 1-continued

| Example | Compound | R¹ | R² | R³ | R⁴ | mp [° C.] | Prepared in accordance with Example |
|---|---|---|---|---|---|---|---|
| | [4.5]dec-1-yl)acetic acid ethyl ester | | | | methyl | | |
| 16 | 5-ethyl-5-phenyl-3[1.3.4]thiadiazol-2-yl-2,4-imidazolidinedione | ethyl | phenyl | H | 1,3,4-thiadiazol-2-yl | 217–220 | 6 |
| 17 | 5-ethyl-3-(5-methylisoxazol-3-yl)-5-phenyl-2,4-imidazolidinedione | ethyl | phenyl | H | 5-methylisoxazol-3-yl | 156–157 | 6 |
| 18 | 3-(5-tert.-butyl-1.3.4]thiadiazol-2-yl]-5-ethyl-5-phenyl-2,4-imidazolidinedione | ethyl | phenyl | H | 5-tert.-butyl[1.3.4]-thiadiazol-2-yl | 145–146 | 6 |
| 19 | 5-ethyl-5-phenyl-3-pyridin-4-yl-2,4-imidazolidinedione | ethyl | phenyl | H | pyridin-4-yl | 153–154 | 6 |
| 20 | 5-ethyl-5-phenyl-3-pyrazin-2-yl-2,4-imidazolidinedione | ethyl | phenyl | H | pyrazin-2-yl | 174–176 | 6 |
| 21 | 5-ethyl-5-phenyl-3-pyridin-3-yl-2,4-imidazolidinedione | ethyl | phenyl | H | pyridin-3-yl | 158–160 | 6 |
| 22 | 3-pyridin-4-yl-1,3-diazaspiro[4.5]-decane-2,4-dione | pentamethylene | | H | pyridin-4-yl | 252–254 | 6 |
| 23 | 3-pyridin-3-yl-1,3-diazaspiro[4.5]-decane-2,4-dione | pentamethylene | | H | pyridin-3-yl | 248–249 | 6 |
| 24 | 3-benzo[1.2.5]-thiadiazol-4-yl-5-ethyl-5-phenyl-2,4-imidazolidinedione | ethyl | phenyl | H | benzo[1.2.5]-thiadiazol-4-yl | 154–156 | 6 |
| 25 | 5-ethyl-5-phenyl-3-(5-trifluoromethyl[1.3.4]thiadiazol-2-yl)-2,4-imidazolidinedione | ethyl | phenyl | H | 5-trifluoromethyl[1.3.4]-thiadiazol-2-yl | 118–120 | 6 |
| 26 | 3-(4,6-dimethylpyridin-2-yl)-5-ethyl-5-phenyl-2,4-imidazolidinedione | ethyl | phenyl | H | 4,6-dimethylpyridin-2-yl | 141–142 | 1A |
| 27 | 5-ethyl-5-phenyl-3-(4-phenyl-thiazol-2-yl)-2,4-imidazolidinedione | ethyl | phenyl | H | 4-phenyl-thiazol-2-yl | 118–120 | 1A |
| 28 | 5-ethyl-3-(3-methylisoxazol-5-yl)-5-phenyl-2,4-imidazolidinedione | ethyl | phenyl | H | 3-methylisoxazol-5-yl | 146–148 | 6 |

The enantiomers shown in Table 2 were obtained in the form of viscous oils by resolving the racemates from Examples 17, 18 and 28 under the conditions described in Example 5. Methanol was used as the solvent for the determination of the angle of rotation $[\alpha]^{RT}_D$.

TABLE 2

| Example | Compound | $[\alpha]_D^{RT}$ |
|---|---|---|
| 29 | (+)-5-ethyl-3-(5-methylisoxazol-3-yl)-5-phenyl-2,4-imidazolidinedione | +36.2° |
| 30 | (−)-5-ethyl-3-(5-methylisoxazol-3-yl)-5-phenyl-2,4-imidazolidinedione | −36.4° |
| 31 | (+)-3-(5-tert.-butyl[1.3.4]thiadiazol-2-yl)-5-ethyl-5-phenyl-2,4-imidazolidinedione | +26.0° |
| 32 | (−)-3-(5-tert.-butyl[1.3.4]thiadiazol-2-yl)-5-ethyl-5-phenyl-2,4-imidazolidinedione | −26.1° |
| 33 | (+)-5-ethyl-3-(3-methylisoxazol-5-yl)-5-phenyl-2,4-imidazolidinedione | +18.5° |
| 34 | (−)-5-ethyl-3-(3-methylisoxazol-5-yl)-5-phenyl-2,4-imidazolidinedione | −18.2° |

Pharmacological Investigations

The release of TNF-α may be investigated in vitro on human mononuclear cells from the peripheral blood (T cells, B cells and monocytes) after stimulation with lipopolysaccharide (LPS) (see below under point 1.). LPS is a bacterial cell wall component and stimulates monocytes and macrophages.

In addition to stimulation with LPS, the release of TNF-α may also be induced by stimulating human mononuclear cells from the peripheral blood with T cell-specific, monoclonal antibodies against activation antigens (antiCD2/antiCD28) or the bacterial superantigen toxic shock syndrome toxin-1 (TSST-1). Apart from the release of TNF-α, these stimulants also inter alia bring about the formation of interleukin 2 (IL-2). Compounds having a general immunosuppressive action inhibit the release of both TNF-α and IL-2. In contrast, compounds which do not block cellular immune defences, should effectively inhibit LPS-stimulated release of TNF-α, but only slightly inhibit the T cell-specific stimulated release of IL-2 (see below under point 2.).

1. Action on TNF-α release (in vitro)

The inhibitory action of the compounds according to the invention with regard to the release of TNF-α was investigated by in vitro testing with mononuclear cells.

Mononuclear cells were obtained from heparinised blood from at least three voluntary donors. To this end, 20 ml portions of blood were separated over a Ficoll-Paque gradient. The cells were harvested and washed three times with a cell culture medium. The cell culture medium used consisted of RPMI 1640 medium with 2 mM of glutamine (Life Technologies, Eggenstein) supplemented with 10% foetal calf serum (Life Technologies), 50 μg/ml of streptomycin (Sigma, Deisenhofen), 50 IU/ml of penicillin (Sigma) and 100 μM of β-mercaptoethanol (Merck, Darmstadt). The mononuclear cells were then resuspended in 15 ml of cell culture medium and divided into 1 ml portions on a 24 hole incubation plate (Sigma). 1 μl of dimethyl sulphoxide (DMSO, Merck) was added to each of the 1 ml portions used as the control portions. 1 μl of a solution of a compound according to the invention (in DMSO; final concentration in test: 0.5; 5; 12.5 and 50 μg/ml) were added to the test portions. The portions were incubated for 1 hour in a $CO_2$ incubation cabinet (5% $CO_2$, 90% atmospheric humidity). 2.5 μg of LPS (from E. coli 0127:B8; Sigma, Deisenhofen) were then added to each portion, with the exception of the control portion, as a stimulant. The portions were incubated for a further 20 hours. Following incubation, the TNF-α concentration in the cell culture supernatants was determined by ELISA assays (Boehringer-Mannheim). The extent of inhibition of TNF-α release was calculated from the values measured for the control portions and the values for the test portions incubated with the compounds according to the invention. The concentration giving rise to 50% inhibition of TNF-α release ($IC_{50}$ values) was determined by means of a regression curve.

All the compounds according to the invention used exhibited a marked inhibitory action on the LPS-stimulated release of TNF-α. The results are shown in Table 3 below.

TABLE 3

Action on LPS-stimulated TNF-α release (mean and standard deviation)

| Compound according to the invention produced in accordance with Example | Inhibition of TNF-α release in % at a final test concentration of 50 μg/ml | $IC_{50}$ [μg/ml] |
|---|---|---|
| 1 | 83 ± 8 | |
| 2 | 66 ± 18 | 31 |
| 3 | 80 ± 12 | |
| 4 | 90 ± 3 | 8 |

TABLE 3-continued

Action on LPS-stimulated TNF-α release (mean and standard deviation)

| Compound according to the invention produced in accordance with Example | Inhibition of TNF-α release in % at a final test concentration of 50 μg/ml | $IC_{50}$ [μg/ml] |
|---|---|---|
| 5 (+) isomer | 93 ± 6 | 4 |
| 5 (−) isomer | 74 ± 16 | 10 |
| 6 | 74 ± 19 | |
| 8 | 48 ± 14 | |
| 10 | 76 ± 9 | 9 |
| 11 | 70 ± 16 | |
| 13 | 73 ± 13 | 24 |
| 14 | 74 ± 6 | |
| 15 | 78 ± 14 | |
| 16 | 69 ± 8 | |
| 18 | 65 ± 29 | |
| 19 | 92 ± 4 | <1 |
| 20 | 87 ± 3 | 5 |
| 22 | 80 ± 7 | |
| 23 | 68 ± 6 | |
| 24 | 89 ± 4 | |
| 25 | 49 ± 13 | |
| 26 | 71 ± 8 | |
| 27 | 73 ± 20 | |
| 29 | 87 ± 4 | 7 |
| 30 | 61 ± 6 | |
| 31 | 68 ± 11 | |
| 33 | 92 ± 4 | 6 |

2. Action on Cellular Immune Defences (in vitro)

Differently stimulated mononuclear cells were used in the series of in vitro tests described below in order to investigate the action of the compounds according to the invention on cellular immune defences.

Compounds according to the invention were investigated with regard to their action on the release of TNF-α and IL-2. The tests were performed under the conditions described under point 1.. The stimulants were changed for each series of tests. The stimulants used were either monoclonal antibodies antiCD2/antiCD28, superantigen TSST-1 or LPS.

The stimulants were adjusted to the following final concentrations:

| | |
|---|---|
| antiCD2/antiCD28: | 100 ng/ml of AICD2.M1; 100 ng/ml of AICD2.M2 (monoclonal antibodies, both directed against CD2, supplied by Deutsches Krebsforschungszentrum, Prof. Dr. Meuer, Heidelberg); 0.1% (vol/vol) antiCD28 Ascites fluid (CLB, Amsterdam) |
| Superantigen: | 0.1 μg/ml of TSST-1 (Sigma, Deisenhofen) |
| LPS: | 2.5 μg of LPS (from E. coli 0127:B8; Sigma, Deisenhofen) |

The compounds according to the invention were used in concentrations (see Table 4, column 2) which brought about a 60–90% inhibition of LPS-induced TNF-α release.

In the test portions stimulated with the antiCD2/antiCD28 antibody mixture or with superantigen TSST-1, the IL-2 concentration in the cell culture supernatants was tested with ELISA assays (Boehringer-Mannheim) at the end of the test.

The compounds according to the invention used did not bring about a general immunosuppressive effect as, unlike dexamethasone, IL-2 release was only relatively slightly inhibited.

The results are shown in Table 4:

TABLE 4

Action on TNF-α and IL-2 release under different stimulation conditions (mean and standard deviation)

| Compound according to the invention produced in accordance with Example | Concentration used in test | TNF-α inhibition: LPS stimulated [%] | IL-2 inhibition: antiCD2/antiCD28 stimulated [%] | IL-2 inhibition: TSST-1 stimulated [%] |
|---|---|---|---|---|
| Dexamethasone | [5.0 μg/ml] | 86.2 ± 1.5 | 58.3 ± 21.1 | 83.9 ± 14.5 |
| 2 | [50.0 μg/ml] | 66.0 ± 18.1 | 7.3 ± 29.1 | 12.4 ± 15.7 |
| 4 | [50.0 μg/ml] | 92.2 ± 3.1 | 21.2 ± 27.3 | 55.4 ± 8.5 |
| 10 | [12.5 μg/ml] | 61.1 ± 13.9 | 13.2 ± 19.6 | 33.9 ± 6.4 |
| 19 | [5.0 μg/ml] | 73.1 ± 8.9 | 34.8 ± 3.1 | 35.1 ± 2.3 |

3. Antivasculitic Action in Animal Model

The antivasculitic action of the compounds according to the invention of the formula I was characterised in vivo by means of a two-phase model originally based on the local Shwartzman reaction [*Exp. Toxic. Pathol.*, 47, 167, (1995)]. This animal model may be used to detect inhibition of endothelial permeability which is not attributable to inhibition of TNF-α release. It is possible, on the basis of the quantified parameter of endothelial permeability to establish the considerable reduction or absence of the tissue destruction characteristic of the Shwartzman reaction.

Male NMRI mice were briefly anaesthetised and dorsally depilated. 100 μg of lipopolysaccharide (Salmonella typhosa; Sigma, Deisenhofen) or, as a control, physiological saline were injected intradermally at symmetrical points on both sides. 24 hours later, Evans blue (Merck, Darmstadt) was administered via the tail vein at a concentration of 1 ml/kg. Recombinant murine TNF-α (133 ng) was then injected subcutaneously under the two areas of skin sensitised with LPS. Four hours after TNF-α stimulation, the mice were killed and the defined areas of skin stamped out. The content of Evans blue in the skin samples was measured by photometric determination of absorbance at 623 nm following 18 hours' extraction in formamide at 60° C.

The compounds according to the invention were suspended in an aqueous 1% carboxymethylcellulose solution and administered intraperitoneally or orally. In the case of intraperitoneal administration, the compounds according to the invention were administered in each case 10 minutes before administration of the LPS or TNF-α, in the case of oral administration, 30 minutes before these stimuli. The compounds according to the invention were readministered during the preparation phase 8 hours after the LPS injection. Doses were 5–400 mg/kg. Animals were also pretreated with NaCl instead of LPS as a control.

Table 5 shows the maximum inhibitory action in % in animals prepared with LPS and treated with compounds according to the invention in comparison with animals prepared with NaCl and treated with compounds according to the invention. The percentages are mean values of ≧10 animals per group.

The compounds according to the invention exhibit an antivasculitic action which could be quantified by detection of inhibition of endothelial permeability. The results are shown in Table 5.

TABLE 5

Inhibition of endothelial permeability (Evans blue extraction)

| Compound according to the invention produced in accordance with Example | Concentration used in the test [mg/kg] | Maximum inhibition of Evans blue extravasation |
|---|---|---|
| 2 | 3 × 50 | 67% |
| 4 | 3 × 100 | 48% |
| 5 (+)-isomer | 3 × 50 | 38% |
| 5 (−)-isomer | 3 × 100 | 58% |

What is claimed is:

1. A substituted 2,4-imidazolidinedione compound corresponding to the formula I

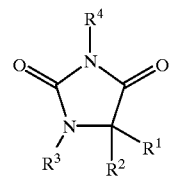

wherein $R^1$ represents $C_{1-6}$ alkyl or $C_{3-6}$ cycloalkyl;

$R^2$ represents $C_{1-6}$ alkyl, phenyl, —$(CH_2)_{1-3}$-phenyl or —$(CH_2)_{1-4}$—$COOR_5$, or $R^1$ and $R^2$ together represent —$(CH_2)_{4-6}$-, —$(CH_2)_2$—O—$(CH_2)_2$- or

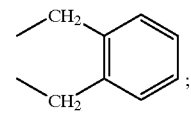

$R^3$ represents H, $C_{1-5}$ alkyl or —$(CH_2)_{1-4}$—$COOR^5$;

$R^4$ represents a heteroaromatic group selected from the formulae:

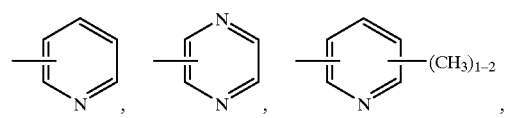

-continued

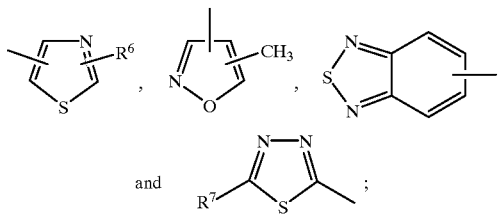

R[5] represents C$_{1-3}$ alkyl;
R[6] represents H, C$_{1-4}$ alkyl, phenyl or benzyl, and
R[7] represents H, C$_{1-4}$ alkyl or trifluoromethyl.

2. A substituted 2,4-imidazolidinedione compound according to claim 1, wherein
R[1] represents C$_{1-4}$ alkyl or C$_{3-4}$ cycloalkyl, and
R[2] represents C$_{3-6}$ alkyl, phenyl, —(CH$_2$)$_{1-2}$-phenyl or —(CH$_2$)$_{1-2}$—COOR[5], or
R[1] and R[2] together represent —(CH$_2$)$_5$- or

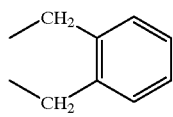

R[3] represents H, C$_{1-4}$ alkyl or —(CH$_2$)$_{1-2}$—COOR[5];
R[4] represents a heteroaromatic group selected from the formulae

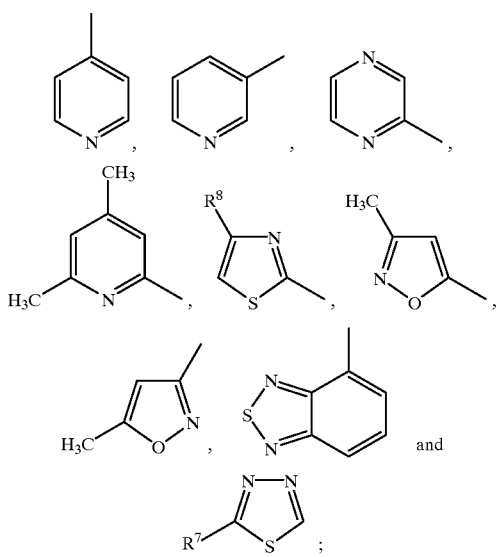

R[5] represents C$_{1-3}$ alkyl;
R[6] represents H or phenyl, and
R[7] represents H, methyl, tert.-butyl or trifluoromethyl.

3. A substituted 2,4-imidazolidinedione compound according to claim 1, wherein
R[1] represents ethyl or cyclobutyl, and
R[2] represents phenyl, or
R[1] and R[2] together represent —(CH$_2$)$_5$-.

4. A substituted 2,4-imidazolidinedione compound according to claim 1, wherein R[1] and R[2] together represent —(CH$_2$)$_5$-.

5. A substituted 2,4-imidazolidinedione compound according to claim 1, wherein

R[3] represents H, C$_{1-3}$ alkyl or —CH$_2$—COOR[5], and
R[5] represents ethyl.

6. A substituted 2,4-imidazolidinedione compound according to claim 5, wherein R[3] represents H.

7. A substituted 2,4-imidazolidinedione compound according to claim 1, wherein R[4] represents pyridin-4-yl, pyridin-3-yl, thiazol-2-yl, 3-methylisoxazol-5-yl or 5-methylisoxazol-3-yl.

8. A substituted 2,4-imidazolidinedione compound according to claim 7, wherein R[4] represents thiazol-2-yl.

9. A pharmaceutical composition comprising at least one pharmaceutically acceptable carrier or adjuvant and an effective TNF-α release inhibiting amount of a substituted 2,4-imidazolidinedione compound corresponding to the formula I

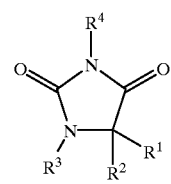

wherein

R[1] represents C$_{1-6}$ alkyl or C$_{3-6}$ cycloalkyl;
R[2] represents C$_{1-6}$ alkyl, phenyl, —(CH$_2$)$_{1-3}$-phenyl or —(CH$_2$)$_{1-4}$—COOR[5,] or
R[1] and R[2] together represent —(CH$_2$)$_{4-6}$-, -(CH$_2$)$_2$-O-(CH$_2$)$_2$- or

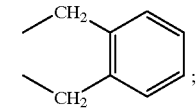

R[3] represents H, C$_{1-5}$ alkyl or —(CH$_2$)$_{1-4}$—COOR[5];
R[4] represents a heteroaromatic group selected from the formulae:

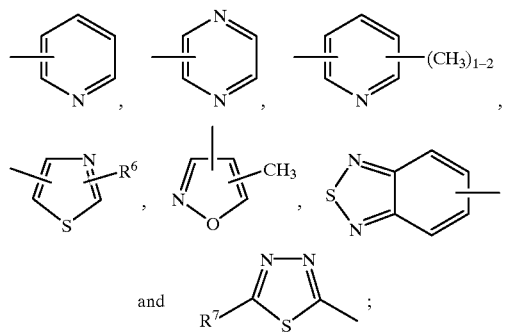

R[5] represents C$_{1-3}$ alkyl;
R[6] represents H, C$_{1-4}$ alkyl, phenyl or benzyl, and
R[7] represents H, C$_{1-4}$ alkyl or trifluoromethyl.

* * * * *